United States Patent  (10) Patent No.: US 8,395,120 B2
Pan et al.  (45) Date of Patent: *Mar. 12, 2013

(54) BIDIRECTIONAL OPTICAL SCANNER ASSISTING IN MAMMOGRAPHY

(75) Inventors: Min-Chun Pan, Taoyuan County (TW); Jhao-Ming Yu, Taoyuan County (TW); Hung-Chih Chiang, Chiayi (TW); Min-Cheng Pan, Keelung (TW); Chun-Yu Chen, Taipei County (TW); Liang-Yu Chen, Taoyuan County (TW)

(73) Assignee: National Central University, Taoyuan County (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/351,384

(22) Filed: Jan. 17, 2012

(65) Prior Publication Data

US 2012/0220862 A1 Aug. 30, 2012

Related U.S. Application Data

(63) Continuation-in-part of application No. 13/035,287, filed on Feb. 25, 2011.

(51) Int. Cl.
 *G01J 5/02* (2006.01)
(52) U.S. Cl. ............ 250/339.02; 250/338.1; 250/370.08
(58) Field of Classification Search ............... 250/370.08
 See application file for complete search history.

(56) References Cited

U.S. PATENT DOCUMENTS

| 4,515,165 | A  | * | 5/1985 | Carroll ......................... 600/475 |
| 5,999,836 | A  | * | 12/1999 | Nelson et al. ................. 600/407 |
| 2008/0218727 | A1 | * | 9/2008 | Djeziri et al. .................... 356/2 |
| 2009/0005692 | A1 | * | 1/2009 | Intes et al. .................... 600/477 |
| 2010/0246759 | A1 | * | 9/2010 | Ogura et al. .................... 378/21 |

* cited by examiner

*Primary Examiner* — Marcus Taningco
(74) *Attorney, Agent, or Firm* — Rosenberg, Klein & Lee

(57) ABSTRACT

A bidirectional optical scanner assisting in mammography is revealed. The optical scanner that calculates functional images obtained by diffuse optical tomography, used in combination with a mammography machine can reduce the number of mammograms taken and the dose exposure. The bidirectional optical scanner includes a first compression plate, a first optical detection module, a second optical detection module and a second compression plate. The same test position of the tested breast can be detected twice in different directions by the first and the second optical detection modules. No matter where the tumor is located, the tumor can be detected. Besides structural images provided by the mammography machine, functional tomographic images of the breast are obtained by the bidirectional optical scanner. Thus diagnostic accuracy in the detection of breast cancer is improved.

37 Claims, 12 Drawing Sheets

BIDIRECTIONAL OPTICAL SCANNER ASSISTING IN MAMMOGRAPHY

REFERENCE TO RELATED APPLICATION

This application is being filed as a Continuation-in-Part of patent application Ser. No. 13/035,287, filed 25 Feb. 2011, currently pending.

BACKGROUND OF THE INVENTION

1. Fields of the Invention

The present invention relates to a bidirectional optical scanner, especially to a bidirectional optical scanner assisting in mammography with improved accuracy of breast cancer diagnosis.

2. Descriptions of Related Art

Breast cancer, the most common cancer in women, caused 500,000 deaths per year worldwide. In western countries, breast cancer afflicts 25 percent of all female cancer patients. According to a medical paper published in Taiwan 2003, breast cancer is the fourth most common cause of female cancer death.

The peak age of breast cancer in oriental women is around 40-50 years old, while that in the western countries is around 30-40. Compared with other cancers, breast cancer is easier to be detected at an early stage. When people feel a lump in the breast, some are reluctant to acknowledge the presence and afraid to have surgery. Thus they tend to delay the treatment. In fact, most breast lumps are benign and many choices are available for the treatment of breast cancer beside removal of the whole breast. In recent clinical practice, the average 10-year disease-free survival rate is 60%. The average 10-year breast cancer survival rate for stage 1 breast cancer with best treatment is 80%. Treatment for stage 0 breast cancer is very successful and the survival rate for stage 0 is nearly 100%. Therefore, early detection and treatment of breast cancer are very important.

Self-examination and doctor's touch are both regular examinations of women's breasts to detect breast cancer earlier. Once abnormal changes are observed, further image analysis is required. The medical ultrasonic Imaging system and mammography are used as diagnostic and screening tools for detecting early breast cancer. They are also used as criterions while making comparison with other breast imaging techniques. In routine examinations, medical ultrasonic Imaging is used for first visit due to the properties of real-time imaging and low cost. As to the mammography, it is a useful screening tool because it detects micro-calcification clusters with high sensitivity and the lesion is detected earlier. Another technique-magnetic resonance imaging (MRI), the widespread of this technique is limited by the high cost of the instrument and the exam. Yet the image resolution of the MRI is higher than the above two techniques and the MRI provides functional imaging.

Like other X-ray tests, mammography uses low-dose ionizing radiation to penetrate the body and create an image. The image is analyzed by radiologists. However, mammography has encountered opposition from the medical professionals due to the high false rate and the radiation does during the test. The false-negative rate of the mammography is at least 10%. The false-negative means a result that appears negative but fails to reveal a condition of having cancer. This is due to dense tissues obscuring the small tumor and the fact that the appearance of cancer on mammograms has a large overlap with the appearance of normal tissues. Some other women are given a false-positive (showing abnormalities, but not cancer) mammogram result.

In order to solve the above problems, there is a need to provide a device assisting in mammography for fewer mammograms and reducing dose exposure.

SUMMARY OF THE INVENTION

Therefore it is a primary object of the present invention to provide a bidirectional optical scanner used as an aid in mammography for reducing the number of mammograms taken and lowering the dose exposure.

It is another object of the present invention to provide a bidirectional optical scanner that detects the same test position of a tested breast twice in two directions. Thus the breast cancer can be detected no matter where it is located. Moreover, besides conventional structural images provided by mammography, the present invention provides functional tomographic images of the tested breast so as to enhance the diagnostic accuracy of breast cancer.

It is a further object of the present invention to provide a bidirectional optical scanner that detects breast cancer over a large area with improved detection speed and reduced detection time.

It is a further object of the present invention to provide a bidirectional optical scanner that is moveable to get images, not limited by the shape of the tested breast. Thus the bidirectional optical scanner can detect tumor cells in different shapes of breast.

In order to achieve above objects, the bidirectional optical scanner of the present invention includes a first compression plate, a first optical detection module disposed over the first compression plate, a second optical detection module arranged corresponding to the first optical detection module, and a second compression plate. The first optical detection module includes at least one light source module and at least one detection module. The light source module is formed by a plurality of light emitting elements arranged in a line. The detection module is composed of a plurality of photosensors set in a line. One of the light emitting elements is aligned with corresponding photosensor to form a row. The second optical detection module also includes at least one light source module and at least one detection module. The light source module having a plurality of light emitting elements arranged in a line while the detection module includes a plurality of photosensors set in a line. Each light emitting elements is aligned with corresponding photosensor to form a row. The light emitting elements of the light source module of the second optical detection module are corresponding to the photosensors of the detection module of the first optical detection module. The photosensors of the detection module of the second optical detection module are corresponding to the light emitting elements of the light source module of the first optical detection module. The second compression plate is disposed on the second optical detection module, located between the first optical detection module and the second optical detection module.

Another bidirectional optical scanner arranged at a mammography machine according to the present invention includes a first movement module, a first optical detection module, a second movement module, a second optical detection module, and a second compression plate. The first movement module is set on a first compression plate of the mammography machine and the first optical detection module is disposed on the first movement module. The second movement module is arranged at a loading platform of the mammography machine and corresponding to the first movement module. The second optical detection module is disposed on the second movement module while the second compression plate is set on the second optical detection module. The first compression plate presses a breast set on the second compression plate, allowing the first optical detection module and the second optical detection module carrying out tests on the breast.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1:
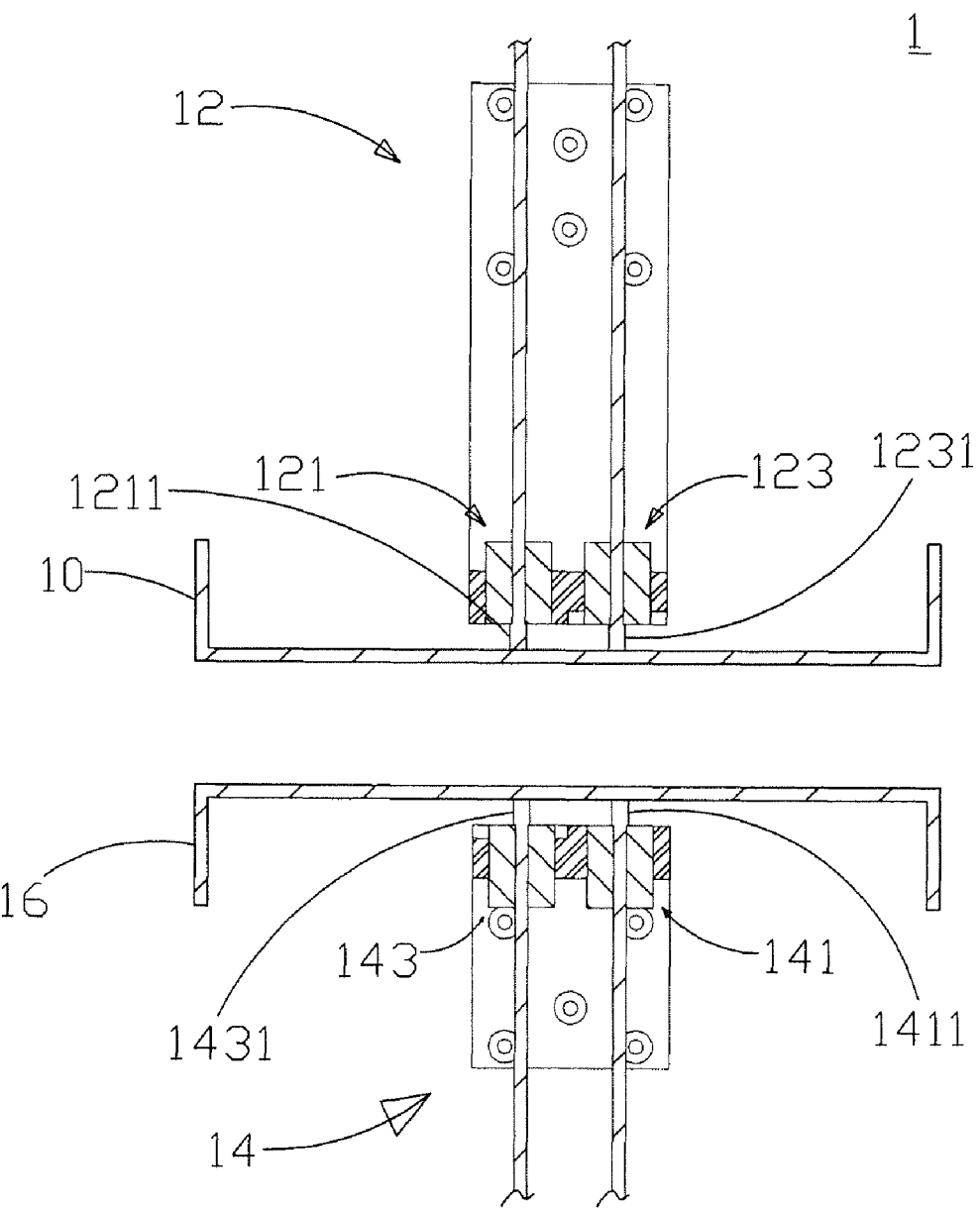
FIG. 1 is a cross sectional view of an embodiment according to the present invention.

Refer to FIG. 1, a cross sectional view of a bidirectional optical scanner 1 is revealed. The bidirectional optical scanner 1 used for breast cancer diagnosis includes a first compression plate 10, a first optical detection module 12, a second optical detection module 14 and a second compression plate 16. The first compression plate 10 is disposed over the second compression plate 16. The first compression plate 10 and the second compression plate 16 are used for pressing a breast to be detected for convenience of performing tests.

Figure 2:
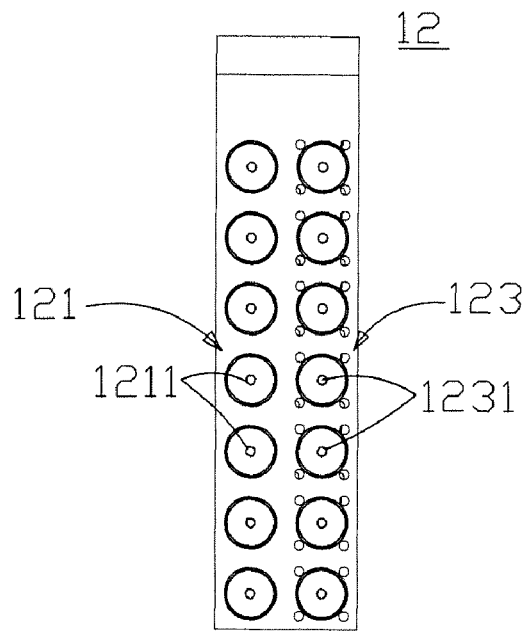
FIG. 2 is a schematic drawing showing an embodiment of a first optical detection module according to the present invention.

The first optical detection module 12 is disposed over the first compression plate 10. Also refer to FIG. 2, a schematic drawing showing an embodiment of the first optical detection module 12 is revealed. The first optical detection module 12 includes a light source module 121 and a detection module 123. The light source module 121 is composed of a plurality of light emitting elements 1211 arranged in a line. Each light emitting element 1211 is an optical fiber that emits laser light or broadband light. The wavelength of the laser light or the broadband light is near infrared wavelength. The detection module 123 includes a plurality of photosensors 1231 arranged in a line and each photosensor 1231 is an optical fiber. The optical fiber generates an optical signal and the optical signal is sent to a signal processing module. The light emitting elements 1211 of the light source module 121 and the photosensors 1231 of the detection module 123 are arranged in an array. The light emitting elements 1211 and the photosensors 1231 respectively are arranged in a line and each light emitting element 1211 is aligned with the corresponding photosensor 1231 to form a row.

Figure 3:
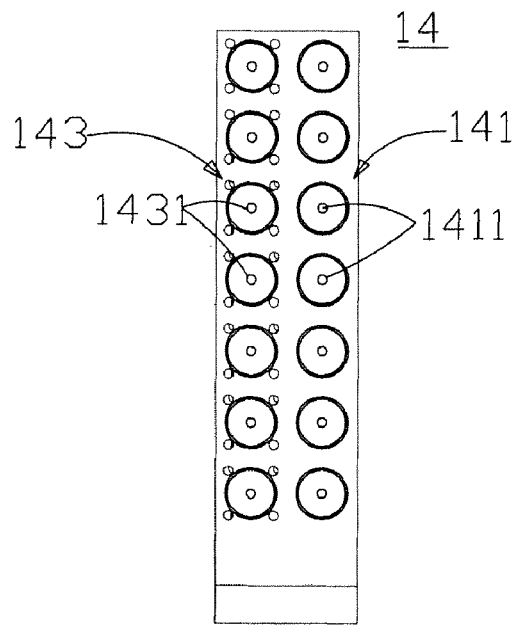
FIG. 3 is a schematic drawing showing an embodiment of a second optical detection module according to the present invention.

Refer to FIG. 3, a schematic drawing showing an embodiment of a second optical detection module 14 is disclosed. As shown in figure, the second optical detection module 14 is disposed under the second compression plate 16. The second optical detection module 14 also includes a light source module 141 and a detection module 143. The light source module 141 includes a plurality of light emitting elements 1411 and each light emitting element 1411 is an optical fiber that emits laser light or broadband light. The wavelength of the laser light or broadband light is near infrared wavelength. The detection module 143 includes a plurality of photosensors 1431 and each photosensor 1431 is an optical fiber. The optical fiber generates an optical signal and the optical signal is sent to a signal processing module. The light emitting elements 1411 of the light source module 141 and the photosensors 1431 of the detection module 143 are arranged in an array. The light emitting elements 1411 and the photosensors 1431 respectively are arranged in a line and each light emitting element 1411 is aligned with the corresponding photosensor 1431 to form a row.

The light source module 141 of this embodiment is corresponding to the detection module 123 of the first optical detection module 12. Each light emitting element 1411 of the light source module 141 is corresponding to each photosensor 1231 of the detection module 123. Similarly, the detection module 143 is corresponding to the light source module 121 of the first optical detection module 12. Each photosensor 1431 of the detection module 143 is corresponding to each light emitting element 1211 of the light source module 121. Thus the number of the light emitting element 1211 of the light source module 121 of the first optical detection module 12 is equal to the number of the photosensor 1431 of the detection module 143 of the second optical detection module 14. The number of the photosensor 1231 of the detection module 123 of the first optical detection module 12 is equal to the number of the light emitting element 1411 of the light source module 141 of the second optical detection module 14. The larger the number of the light emitting element 1211, 1411 of the light source module 121, 141 of the first and the second optical detection modules 12, 14, and the photosensor 1231, 1431 of the detection modules 123, 143, the higher accuracy of diagnostic imaging of the bidirectional optical scanner 1 is.

Figure 4A:
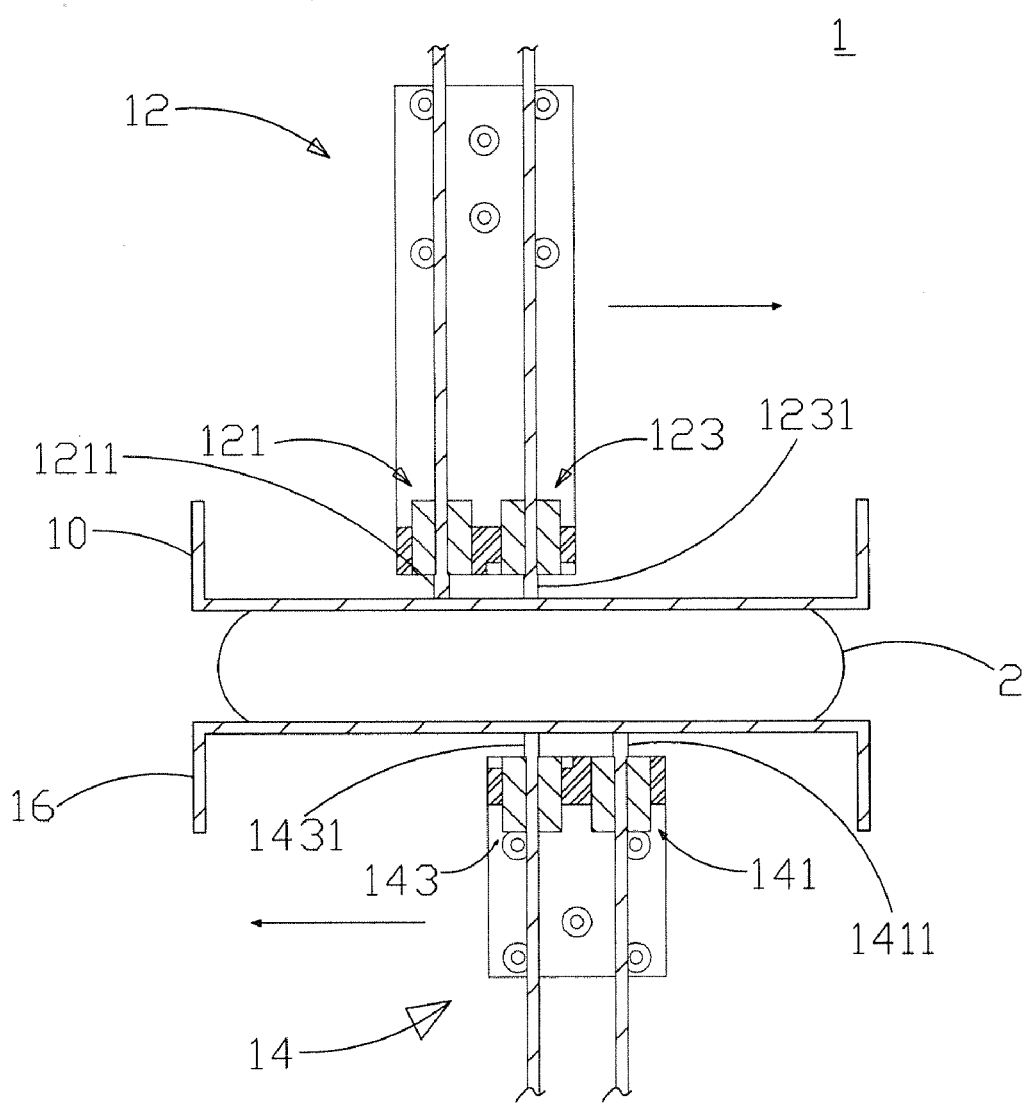
FIG. 4A and FIG. 4B are schematic drawings showing an embodiment in use according to the present invention.
Figure 4B:
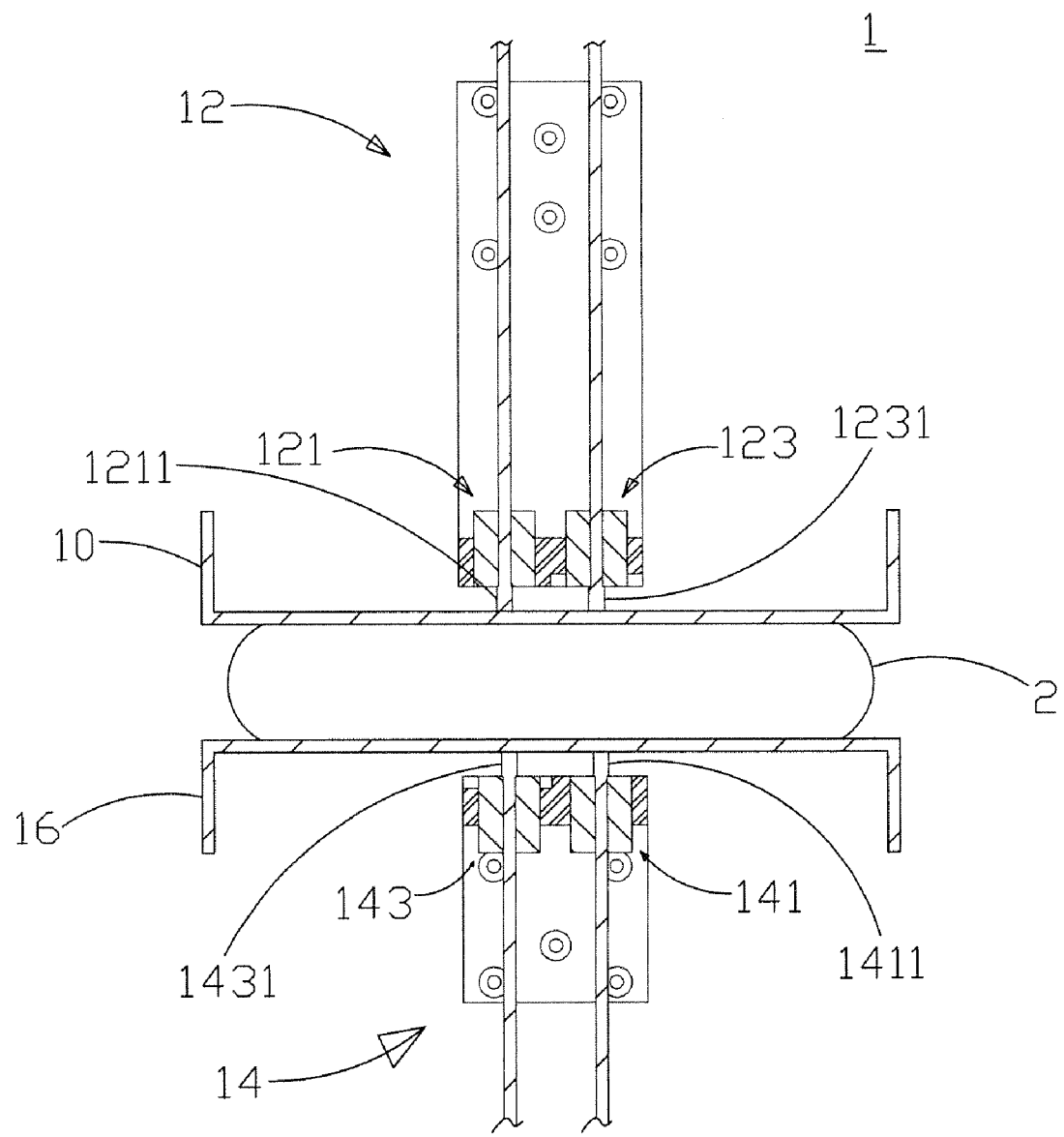

Refer to FIG. 4A and FIG. 4B, while taking breast images by the bidirectional optical scanner 1 of the present invention, one breast 2 to be tested of a patient is set on the second compression plate 16. Then the breast 2 set on the second compression plate 16 is compressed by the first compression plate 10 and tissue of the breast 2 to be tested is spread out evenly. The test distance is reduced and the test sensitivity is improved.

Each light emitting element 1211 of the light source module 121 of the first optical detection module 12 emits light to a plurality of test positions on the tested breast 2 compressed by the first compression plate 10 and the second compression plate 16. The test positions are determined according to the light emitting elements 1211 of the light source module 121 and the photosensors 1231 of the detection modules 123 of the first optical detection module 12, and the light emitting elements 1411 of the light source module 141 and the photosensors 1431 of the detection module 143 of the second optical detection module 14.

Each light emitting element 1211 of the light source module 121 of the first optical detection module 12 emits light to the test positions on the tested breast 2. Light transmits through the test positions on the tested breast 2, and generate transmission photons in the test positions on the tested breast 2. Each photosensor 1431 of the detection module 143 of the second optical detection module 14 receives the transmission photons from the corresponding test position and generates an optical signal.

Simultaneously, each light emitting element 1211 emits light, and light transfers to the test positions on the tested breast 2 to generate reflected photons in the test positions on the tested breast 2. Each photosensor 1231 of the detection module 123 of the first optical detection module 12 receives the reflected photons from the corresponding test position and generates another optical signal. The optical signals from corresponding test positions are converted into a plurality of electrical signals by the photosensors 1231, and the electrical signals are also sent to a signal processing module by the photosensors 1231.

Refer to FIG. 4B, the first optical detection module 12 is shifted to the right side while the second optical detection module 14 is shifted to the left side. The light emitting elements 1411 of the light source module 141 of the second optical detection module 14 emit light to a plurality of test positions on the tested breast 2 compressed and generate the transmission photons and the reflected photons in the test positions on the tested breast 2. Each photosensor 1231 of the detection module 123 of the first optical detection module 12 on the top receives the transmission photons from the corresponding test position and generates an optical signal. Simultaneously, each photosensor 1231 of the detection module 123 of the first optical detection module 12 on the bottom receives the reflected photons from the corresponding test position and generates another optical signal. The optical signals from corresponding test positions are converted into a plurality of electrical signals by the photosensors 1231, and the electrical signals are also sent to the signal processing module by the photosensors 1231.

As shown in FIG. 4A, it is learned that the light emitting elements 1211 on the top side of the device emit light through the test positions over the corresponding test position and then photosensors 1431 on the bottom of the device and photosensors 1231 on the top side of the device respectively receives the transmission photons and the reflected photons from the corresponding test positions so as to generate electrical signals corresponding to the test positions.

As shown in FIG. 4B, it is learned that the light emitting elements 1411 on the bottom side of the device emit light through the test positions over the corresponding test position and then the photosensors 1231 on the top side of the device and the photosensors 1431 on the bottom of the device respectively receives the transmission photons and the reflected photons from the corresponding test positions so as to generate electrical signals corresponding to the test positions.

Thus the same test position has been detected twice. The light source on the top emits light to the test position for the first time while the other time, the light source on the bottom projects light through the test position. At last, the electrical signals obtained from the two tests are treated by functional optical image backward process so as to get a correct image of the test position. Then an image of the breast 2 with high resolution is obtained by reconstruction of the correct images of each test position. Therefore, whether there is a tumor inside the breast 2 is checked according to the image of the breast 2.

The tumor may be located at the upper part of the tested breast 2 or at the lower part of the tested breast 2. By the bidirectional optical scanner 1 of the present invention, each test position of the tested breast 2 has been detected two times in two directions. Thus either the tumor on the upper part of the tested breast 2 or the tumor on the lower part of the tested breast 2 can be detected. Compared with structural images provided by mammography, the present invention provides functional tomographic images of the breast so as to enhance the diagnostic accuracy of breast cancer.

Figure 5:
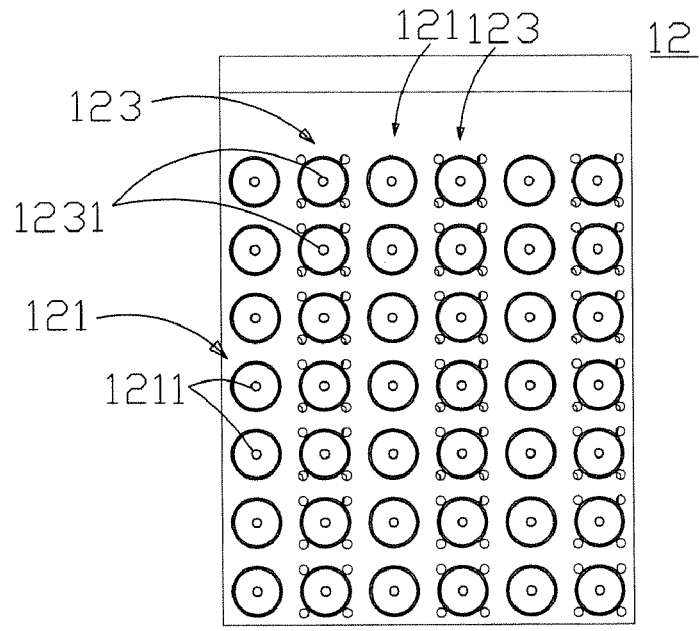
FIG. 5 is a schematic drawing showing another embodiment of a first optical detection module according to the present invention.
Figure 6:
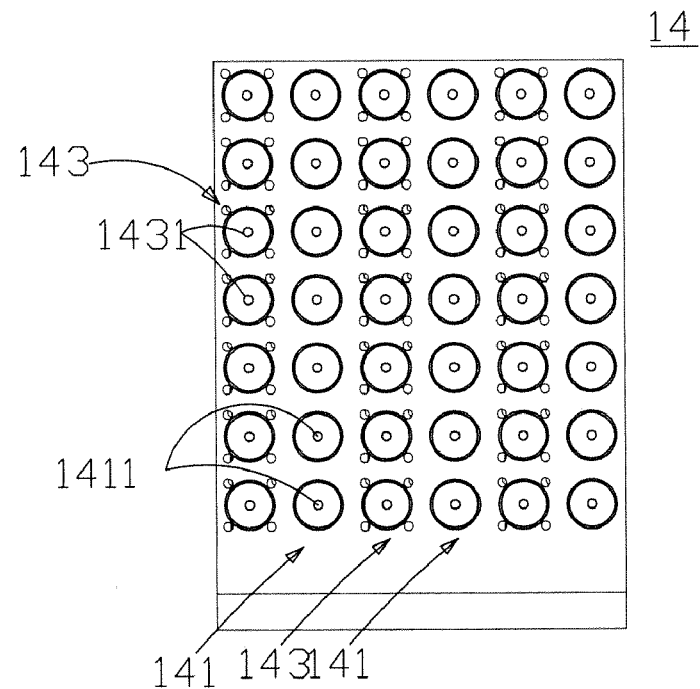
FIG. 6 is a schematic drawing showing another embodiment of a second optical detection module according to the present invention.

Refer to FIG. 5 and FIG. 6, schematic drawings showing another embodiment of the first optical detection module and another embodiment of the second optical detection module are revealed. In the above embodiment, the first optical detection module 12 and the second optical detection module 14 respectively only include one light source module 121, 141 and one detection module 123, 143. In this embodiment, in order to improve detection efficiency and reduce detection time, the first optical detection module 12 and the second optical detection module 14 respectively include a plurality of the light source modules 121, 141 and a plurality of detection modules 123, 143. The light source modules 121, 141 and the detection modules 123, 143 are arranged in turn.

Each light source module 121, 141 includes a plurality of light emitting elements 1211, 1411 arranged in a line. Each detection module 123, 143 includes a plurality of photosensors 1231, 1431 and these photosensors 1231, 1431 are also disposed in a line. When the light source modules 121, 141 and the detection modules 123, 143 are arranged in turn, the light emitting elements 1211, 1411 of the light source modules 121, 141 together with the photosensors 1231, 1431 of the detection modules 123, 143 form an array. In each row of the first optical detection module 12, the light emitting elements 1211 and the photosensors 1231 are arranged alternatively. In similar way, the photosensors 1431 and the light emitting elements 1411 on each row of the second optical detection module 14 are arranged alternatively, in the order of the photosensor 1431, the light emitting element 1411, the photosensor 1431, etc.

Thus the first optical detection module 12 and the second optical detection module 14 are used for large area screening of breast cancer. All of the test positions on the tested breast 2 are detected at one time. Then the first optical detection module 12 and the second optical detection module 14 are moved horizontally so as to detect the test positions of the tested breast 2 once again. Therefore, the detection efficiency is improved and the detection time is reduced significantly.

Figure 7:
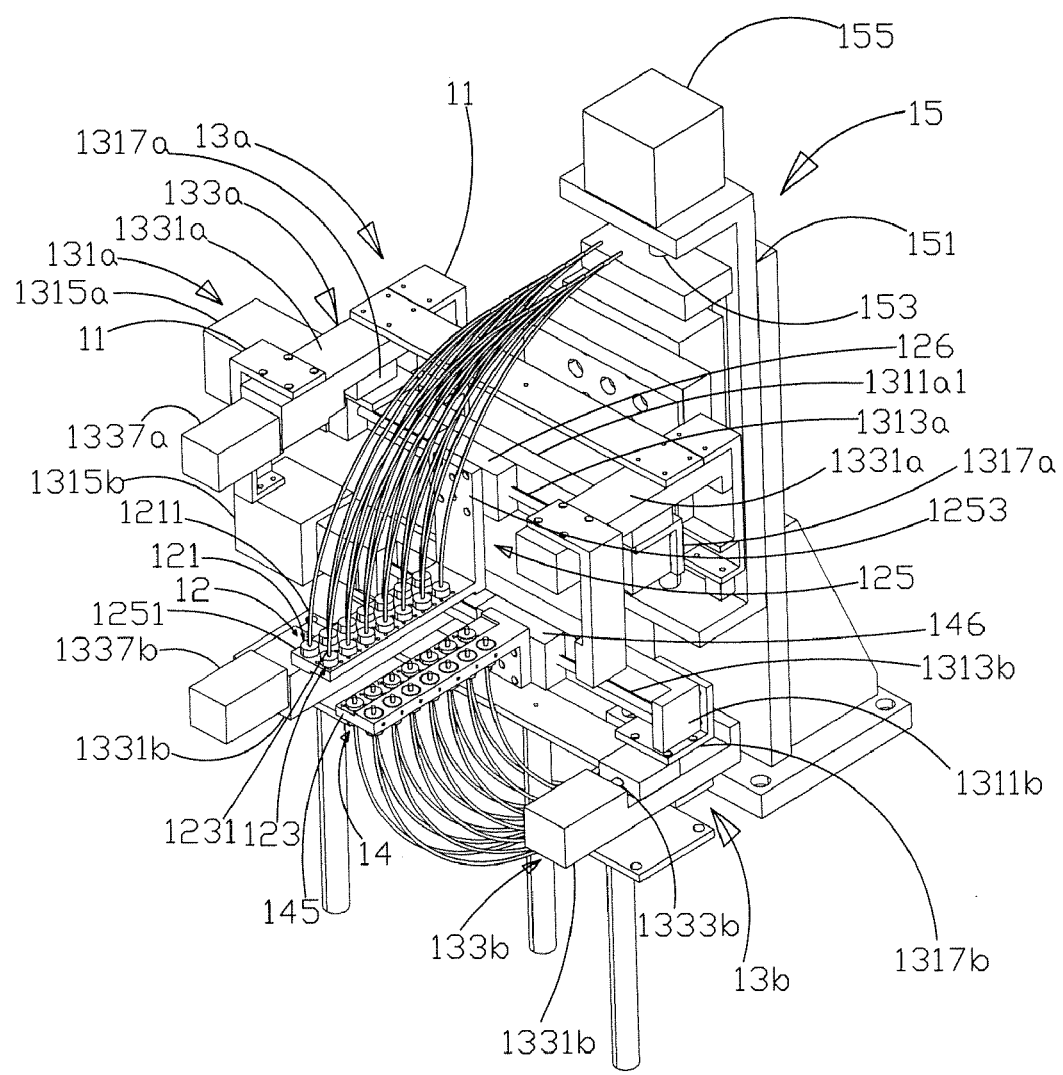
FIG. 7 is a perspective view of a further embodiment according to the present invention.
Figure 8:
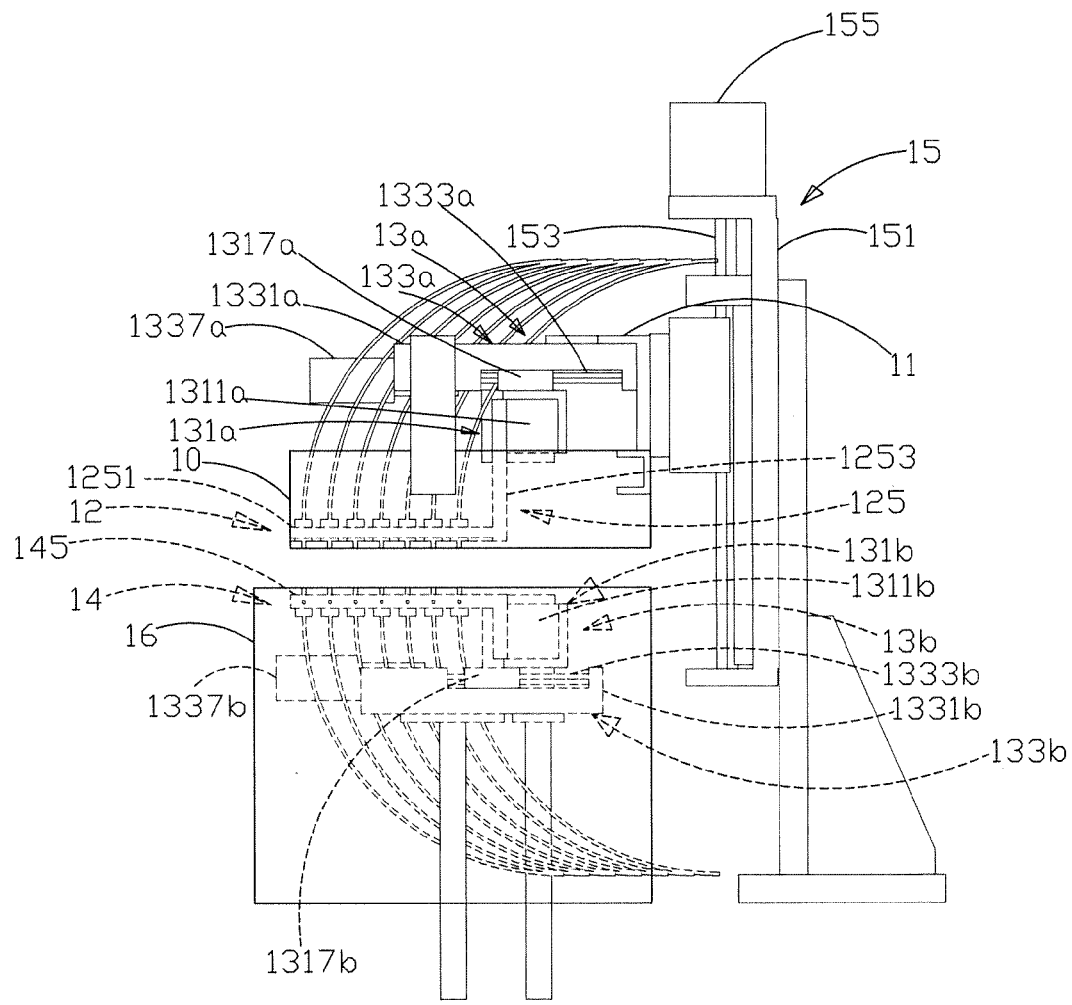
FIG. 8 is a side view of a further embodiment according to the present invention.

Refer to FIG. 7 and FIG. 8, a further embodiment of the present invention is revealed. From the above embodiments, it is learned that the first optical detection module 12 and the second optical detection module 14 should be moved horizontally in order to detect each test position on the tested breast twice. The first optical detection module 12 and the second optical detection module 14 respectively are arranged at a first movement module 13a and a second movement module 13b. The first movement module 13a and a second movement module 13b are mainly used to drive the first optical detection module 12 and the second optical detection module 14 moving in a first direction (the X-direction) and a second direction (the Y-direction).

Take the first optical detection module 12 and the second optical detection module 14 set on the first movement module 13a and the second movement module 13b as examples. The first movement module 13a includes a first moving platform 131a and a second moving platform 133a. The first optical detection module 12 is disposed on the first moving platform 131a. The first moving platform 131a drives the first optical detection module 12 to move in the first direction. The first moving platform 131a arranged with the first optical detection module 12 is disposed on the second moving platform 133a. The second moving platform 133a drives the first optical detection module 12 on the first moving platform 131a moving in the second direction.

The second movement module 13b includes a third moving platform 131b and a fourth moving platform 133b. The second optical detection module 14 is disposed on the third moving platform 131b. The third moving platform 131b arranged with the second optical detection module 14 is disposed on the fourth moving platform 133b. Thus the positions of the first optical detection module 12 and the second optical detection module 14 are adjusted by the first movement module 13a and the second movement module 13b according to the shape of the breast compressed by the first compression plate 10 and the second compression plate 16. Thus the embodiment of the bidirectional optical scanner 1 is not restricted by the shape of the compressed breast in the breast cancer detection, still obtaining a good breast image.

The first moving platform 131a of the first movement module 13a includes a first base 1311a, a first threaded rod 1313a, and a driving device 1315a. The first threaded rod 1313a and the driving device 1315a are arranged at the first base 1311a. The driving device 1315a is connected to the first threaded rod 1313a while the first optical detection module 12 is set on the first threaded rod 1313a. The driving device 1315a is a servo motor. When the driving device 1315a drives the first threaded rod 1313a rotating, the first threaded rod 1313a moves the first optical detection module 12 in the first direction therealong.

The structure of the third moving platform 131b of the second movement module 13b is similar to that of the first moving platform 131a. The third moving platform 131b is composed of a third base 1311b, a third threaded rod 1313b, and a driving device 1315b. The connection way among the third base 1311b, the third threaded rod 1313b and the driving device 1315b is the same with that of the first base 1311a, the first threaded rod 1313a and the driving device 1315a. The second optical detection module 14 is set on the third threaded rod 1313b. When the driving device 1315b drives the third threaded rod 1313b rotating, the third threaded rod 1313b moves the second optical detection module 14 in the second direction therealong.

Moreover, the first optical detection module 12 and the second optical detection module 14 are respectively having a fastener 125, 145. The two fasteners 125, 145 are respectively connected to the first threaded rod 1313a of the first moving platform 131a and the third threaded rod 1313b of the third moving platform 131b. The fastener 125, 145 is L-shaped. Take the fastener 125 of the first optical detection module 12 as an example. The fastener 125 includes a first fixed end 1251 and a second fixed end 1253. The light source modules 121 and the detection modules 123 of the first optical detection module 12 are fixed on the first fixed end 1251 of the fastener 125. The second fixed end 1253 is disposed on the first threaded rod 1313a of the first moving platform 131a. The first optical detection module 12 further includes a sliding block 126 connected to the first threaded rod 1313a. The second fixed end 1253 of the fastener 125 is disposed on the sliding block 126. The disposition of the second fixed end 1253 can be locked or mounted into a locking slot on the sliding block 126. The structure of the fastener 145 and a sliding block 146 of the second optical detection module 14 is the same with that of the fastener 125 and the sliding block 126 of the first optical detection module 12.

The second moving platform 133a and the fourth moving platform 133b are respectively perpendicular to the first moving platform 131a and the third moving platform 131b. The second moving platform 133a is above the first moving platform 131a and the fourth moving platform 133b is under the third moving platform 131b.

Refer to FIG. 7 and FIG. 8, how the second moving platform 133a and the fourth moving platform 133b are disposed on the first moving platform 131a and the third moving platform 131b respectively. The second moving platform 133a is composed of a second base 1331a, two second threaded rods 1333a, and a driving device 1337a. The second base 1331a is above the first moving platform 131a and is perpendicular to the first base 1311a. The two threaded rods 1333a respectively are set on each of two sides of the second base 1331a. The driving device 1337a is disposed on the second base 1331a and is connected to the second threaded rod 1333a. The first base 1311a of the first moving platform 131a is set on the two second threaded rods 1333a. When the driving device 1337a drives the second threaded rod 1333a to rotate, the second threaded rod 1333a further drives the first base 1311a of the first moving platform 131a of the first optical detection module 12 to move. The other second threaded rod 1333a is driven by the first base 1311a and rotating so that the first moving platform 131a moves steadily in the second direction along the second threaded rod 1333a. The first optical detection module 12 is arranged at the first base 1311a of the first moving platform 131a so that the first optical detection module 12 also moves in the second direction along with the first moving platform 131a. The two ends of the first base 1311a of the first moving platform 131a are disposed on the second moving platform 133a by two connection parts 1317a. One end of each connection part 1317a is fixed on the first base 1311a of the first moving platform 131a while the other end of each connection parts 1317a is set on each second threaded rod 1333a.

The fourth moving platform 133b has similar structure to the second moving platform 133a. The fourth moving platform 133b includes a fourth base 1331b, two fourth threaded rods 1333b, and a driving device 1337b. The assembly way of the fourth moving platform 133b is the same with that of the second moving platform 133a. The third base 1311b of the third moving platform 131b is disposed on the two fourth threaded rods 1333b by two connection parts 1317b, the same way as the first base 1311a of the first moving platform 131a set on the two second threaded rods 1333a. Thus the fourth moving platform 133b drives the third moving platform 131b moving in the second direction, further allowing the second optical detection module 14 set on the third moving platform 131b moving in the second direction.

Both the first optical detection module 12 and the second optical detection module 14 move in the first direction and the second direction through the first movement module 13a and the second movement module 13b. Due to the moveable first optical detection module 12 and the moveable second optical detection module 14, the embodiment of the bidirectional optical scanner 1 is not limited by the shape of the breast compressed between the first compression plate 10 and the second compression plate 16, still producing a good image of breast.

Still refer to FIG. 7 and FIG. 8, the movement of both the first optical detection module 12 and the second optical detection module 14 respectively in the first direction and the second direction are controlled by the first movement module 13a and the second movement module 13b. The bidirectional optical scanner 1 further includes a fifth moving platform 15 that controls the movement of the first optical detection module 12 and the first compression plate 10 in the third direction (the Z-direction). While taking a breast image by the bidirectional optical scanner 1, keep the second compression plate 16 still and the breast is set on the still second compression plate 16 firstly, then the first compression plate 10 is moved downward to compress the tested breast.

Thus the fifth moving platform 15 of this embodiment is used to control the movement of the first compression plate 10. Moreover, the first optical detection module 12 is disposed over the first compression plate 10 so that the first optical detection module 12 needs to be moved firstly while moving the first compression plate 10. Thus when the first compression plate 10 is moved upward, the fifth moving platform 15 drives both the first compression plate 10 and the first optical detection module 12 to move upward at the same time. On the other hand, the fifth moving platform 15 also drives the first compression plate 10 and the first optical detection module 12 to move downward at the same time while the first compression plate 10 moving downward.

The fifth moving platform 15 includes a fifth base 151, a fifth threaded rod 153, and a driving device 155. The fifth threaded rod 153 and the driving device 155 are set on the fifth base 151. The driving device 155 is connected to the fifth threaded rod 153 while the first optical detection module 12 and first compression plate 10 are disposed on the fifth threaded rod 153 of the fifth moving platform 15 by a frame 11. Both the first compression plate 10 and the second moving platform 133a are fixed on the frame 11 and the frame 11 is arranged at the fifth threaded rod 153. When the driving device 155 drives the fifth threaded rod 153 to rotate, the fifth threaded rod 153 further drives the frame 11 moving in the third direction. Then the moved frame 11 drives the first compression plate 10 and the first optical detection module 12 to move in the third direction.

Figure 9:
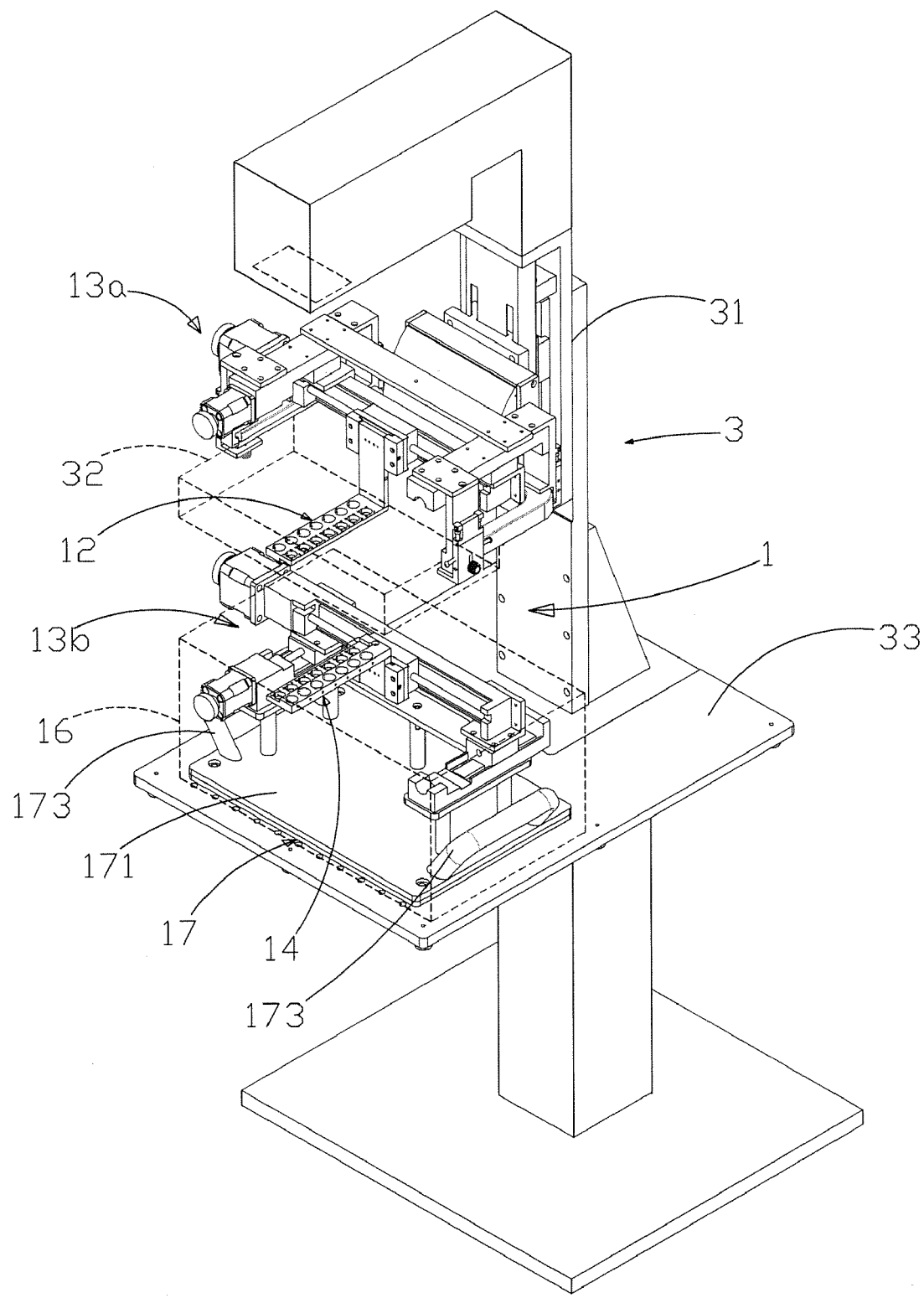
FIG. 9 is a perspective view of a further embodiment according to the present invention.

Refer to FIG. 9, a further embodiment of the present invention is revealed. In this embodiment, the bidirectional optical scanner 1 is arranged at a mammography machine 3 such as an x-ray mammography machine. Generally, the mammography machine 3 includes a lifting mechanism 31, a first compression plate 32 and a loading platform 33. The lifting mechanism 31 is set on the loading platform 33 and the first compression plate 32 is arranged at the lifting mechanism 31. The bidirectional optical scanner 1 includes the first movement module 13a, the first optical detection module 12, the second movement module 13b, the second optical detection module 14 and the second compression plate 16. The first movement module 13a is arranged at the first compression plate 32 of the mammography machine 3 and the first optical detection module 12 is disposed on the first movement module 13a. The fifth moving platform 15 in the above embodiment is replaced by the lifting mechanism 31 of the mammography machine 3 in this embodiment. The first compression plate 32 is driven by the lifting mechanism 31 to move in the third direction (the Z direction). Then the first compression plate 32 drives the first movement module 13a moving upward in the third direction and further drives the first optical detection module 12 moving upward in the third direction.

The second movement module 13b is disposed on the loading platform 33 of the mammography machine 3 and the second optical detection module 14 is arranged at the second movement module 13b. The second compression plate 16 is set on the second optical detection module 14. When the bidirectional optical scanner 1 is disposed on the mammography machine 3, firstly use the bidirectional optical scanner 1 to get images of the breast. Then remove the bidirectional optical scanner 1 from the mammography machine 3. Next the mammography machine 3 takes the image of the breast. Thus the images obtained are compared to improve the diagnostic accuracy of breast cancer effectively.

When the bidirectional optical scanner 1 disposed on the mammography machine 3 is used to get images of the breast, the breast is set on the second compression plate 16 and the first compression plate 32 is moved downward under the control of the lifting mechanism 31 of the mammography machine 3. By compression of the first compression plate 32 and the second compression plate 16 onto the breast, the first optical detection module 12 and the second optical detection module 14 takes images of the breast. The connection among the first movement module 13a, the second movement module 13b, the first optical detection module 12, and the second optical detection module 14 is the same as the above embodiment.

Figure 10:
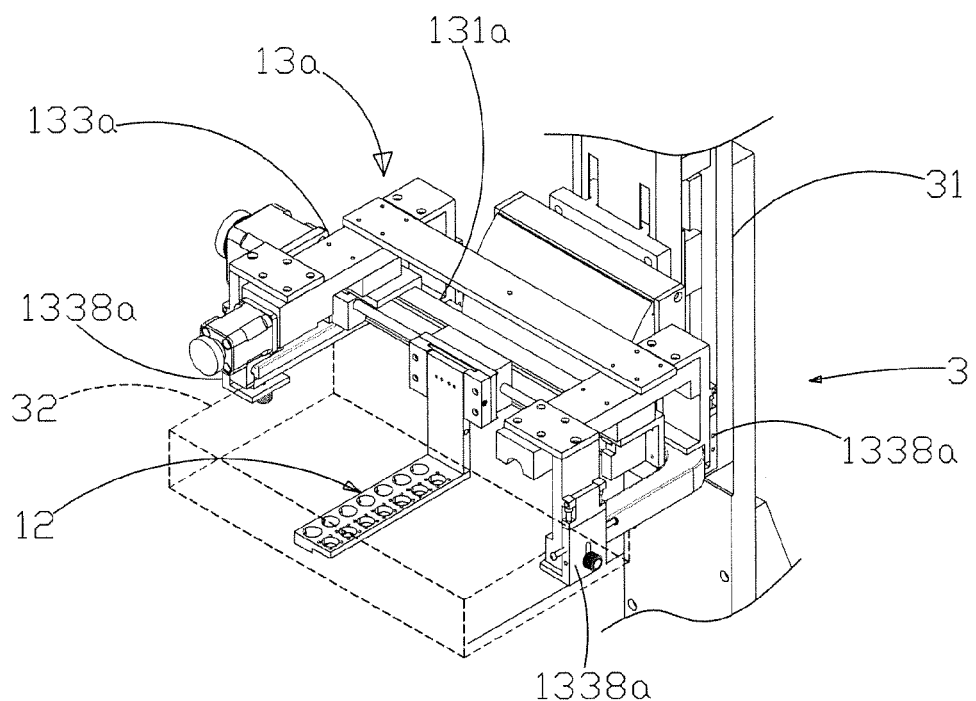
FIG. 10 is a partial enlarged view of a further embodiment according to the present invention.

Refer to FIG. 10, a partial enlarged view of a further embodiment is disclosed. As shown in figure, the first movement module 13a includes the first moving platform 131a and a second moving platform 133a. The first optical detection module 12 is disposed on the first moving platform 131a while the first moving platform 131a is arranged at the second moving platform 133a. The second moving platform 133a includes at least two connection parts 1338a. In this embodiment, there are four connection parts 1338a respectively disposed on a periphery of the second moving platform 133a and fixed on the first compression plate 32 so as to fix the second moving platform 133a on the first compression plate 32. Thus the first movement module 13a is assembled on the first compression plate 32 of the mammography machine 3.

Back to FIG. 9, the second movement module 13b is arranged at a movement base 17 while the movement base 17 is set on the loading platform 33. Thus the second movement module 13b can be arranged at or removed from the loading platform 33 by the movement base 17. The movement base 17 includes a base 171 and two holding parts 173. The two holdings parts 173 are disposed on each of two sides of the base 171 respectively and the base 171 is used to receive the second movement module 13b. Thus users can hold the two holdings parts 173 to move the second movement module 13b easily.

Figure 11:
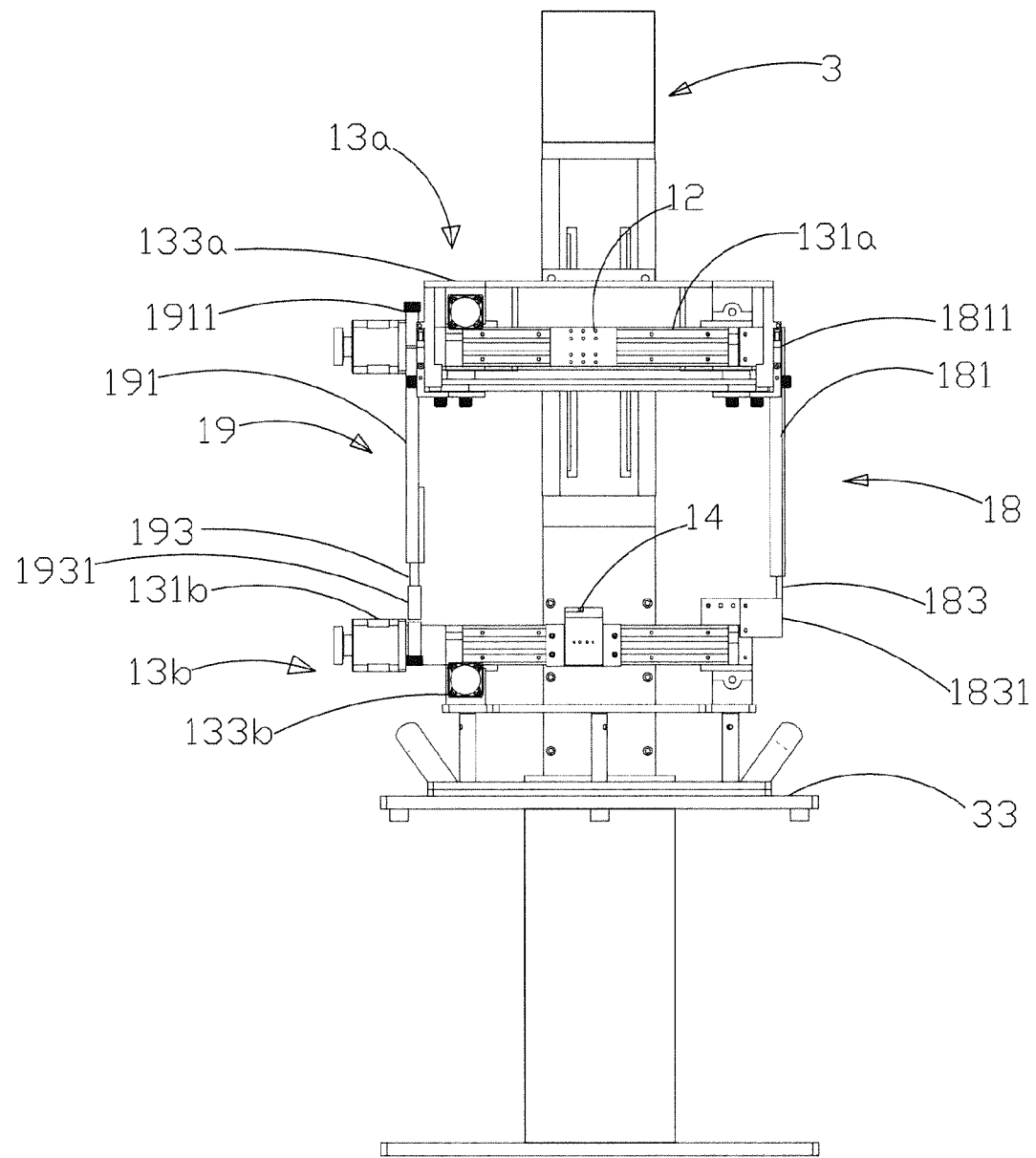
FIG. 11 is a schematic drawing showing structure of a further embodiment according to the present invention.

Refer to FIG. 11, a further embodiment is revealed. As shown in the figure, the first optical detection module 12 and the second optical detection module 14 are respectively disposed on the first movement module 13a and the second movement module 13b when the first movement module 13a and the second movement module 13b are set on the mammography machine 3. In order to position the first optical detection module 12 and the second optical detection module 14, firstly move the first optical detection module 12 and the second optical detection module 14 to one side of the first moving platform 131a and one side of the third moving platform 131b respectively while the first moving platform 131a and the third moving platform 131b respectively are moved to one side of the second moving platform 133a and one side of the fourth moving platform 133b.

Then a positioning mechanism 18 is set between the first moving platform 131a and the third moving platform 131b so as to position the first movement module 13a and the second movement module 13b. The positioning mechanism 18 includes a first positioning part 181 and a second positioning part 183. One end of the first positioning part 181 is disposed with a first clamping part 1811 that holds the first moving platform 131a and the other end of the first positioning part 181 is connected slidingly to one end of the second positioning part 183. The other end of the second positioning part 183 is set with a second clamping part 1831 that holds the third moving platform 131b. When the second optical detection module 14 is disposed on the loading platform 33 of the mammography machine 3, the second positioning part 183 slides in relation to the first positioning part 181 and moves downward until the second movement module 13b is set on the loading platform 33. Moreover, the first positioning part 181 and the second positioning part 183 are perpendicular to the first moving platform 131a and the third moving platform 131b for positioning the first movement module 13a and the second movement module 13b so as to make the first optical detection module 12 and the second optical detection module 14 align with each other.

In order to make the positioning of the first movement module 13a and the second movement module 13b become more precisely, an assisted positioning mechanism 19 is arranged between the first moving platform 131a and the third moving platform 131b. The assisted positioning mechanism 19 includes a first assisted positioning part 191 and a second assisted positioning part 193. One end of the first assisted positioning part 191 is disposed with a first positioning part 1911 that is fixed on the first moving platform 131a and the other end of the first assisted positioning part 191 is connected slidingly to one end of the second assisted positioning part 193. The other end of the second assisted positioning part 193 is set with a second positioning part 1931 that is fixed on the third moving platform 131b. When the second movement module 13b is disposed on the loading platform 33 of the mammography machine 3, the second assisted positioning part 193 slides in relation to the first assisted positioning part 191 and moves downward until the second movement module 13b is set on the loading platform 33. Furthermore, the first assisted positioning part 191 and the second assisted positioning part 193 are perpendicular to the first moving platform 131a and the third moving platform 131b for positioning the first movement module 13a and the second movement module 13b. Thus the assisted positioning mechanism 19 is used in combination with the positioning mechanism 18 for positioning the first movement module 13a and the second movement module 13b precisely and aligning the first optical detection module 12 with the second optical detection module 14.

Figure 12:
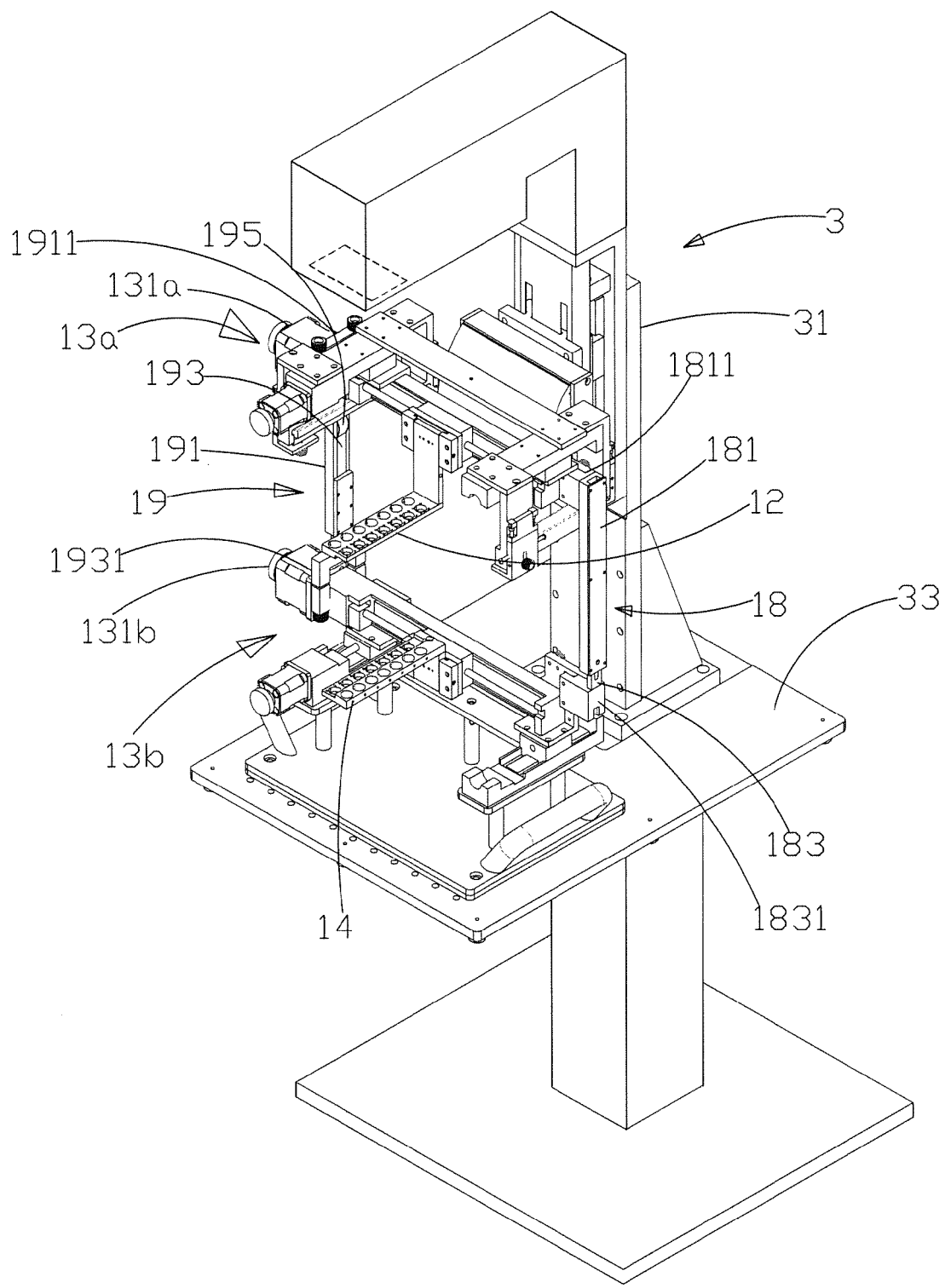
FIG. 12 is a perspective view of a further embodiment according to the present invention.

Refer to FIG. 12, a further embodiment is revealed. An alarm part 195 is set between the first assisted positioning part 191 and the second assisted positioning part 193. When both the first movement module 13a and the second movement module 13b are positioned, the first movement module 13a can move toward the second movement module 13b and the first assisted positioning part 191 slides downward so that the alarm part 195 is compressed. Users can check whether the first movement module 13a and the second movement module 13b are already positioned precisely according to the degree of the compression of the alarm part 195.

Figure 13:
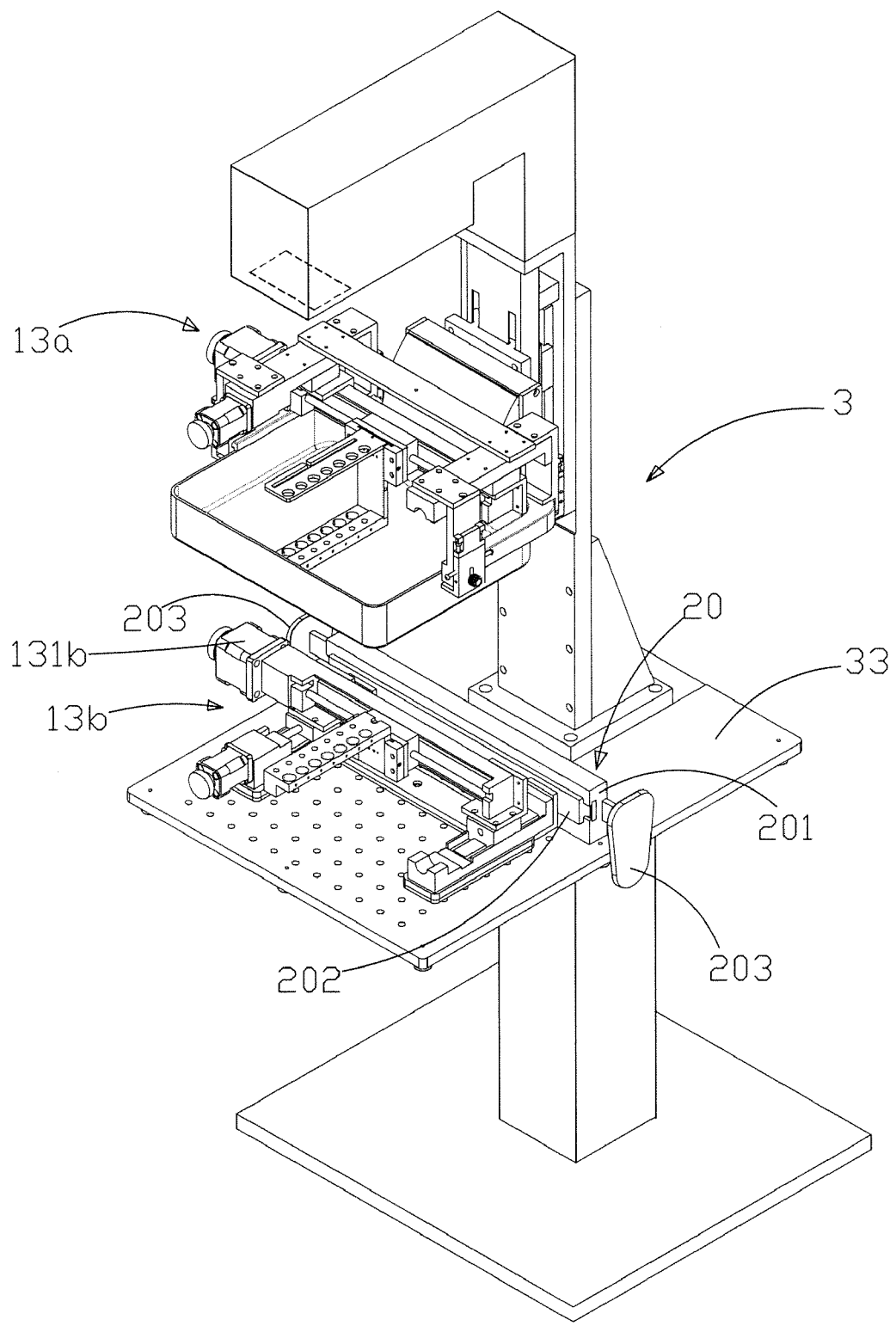
FIG. 13 is a perspective view of a further embodiment according to the present invention.

Refer to FIG. 13, a further embodiment is disclosed. In the above embodiment, the second movement module 13b is set on the movement base 17. For getting a mammogram by the mammography machine 3, users need to move the movement base 17 with their hands to remove the second movement module 13b from the loading platform 33. In this embodiment, the second movement module 13b is set on a linear guideway positioning module 20. The second movement module 13b is moved along the linear guideway positioning module 20 on the loading platform 33. The linear guideway positioning module 20 includes a linear guideway 201, a loading frame 202 and two positioning parts 203. The two positioning parts 203 are respectively arranged at each of two ends of the linear guideway 201. The loading frame 202 is sliding within the linear guideway 201 and is used for receiving the third moving platform 131b of the second movement module 13b. The two positioning parts 203 can be pulled out of the linear guideway 201 or retracted therein. The two positioning parts 203 are respectively fixed on each of two ends of the loading platform 33.

While getting a mammogram by the mammography machine 3, the second movement module 13b should be removed from the loading platform 33. In this embodiment, the second movement module 13b is removed from the loading platform 33 through the linear guideway positioning module 20. The third moving platform 131b of the second movement module 13b is disposed on the loading frame 202 that is sliding inside the linear guideway 201. Thus the loading frame 202 drives the third moving platform 131b to move and further drives the second movement module 13b to move. Therefore the second movement module 13b is removed from the loading platform 33, allowing the mammography machine 3 to get mammograms. While using the bidirectional optical scanner 1 to get images, the second movement module 13b is moved back to the loading platform 33 by means of the linear guideway positioning module 20. The linear guideway positioning module 20 can also help the second movement module 13b make minor adjustment during positioning processes so that the first movement module 13a and the second movement module 13b are positioned more precisely.

In summary, the bidirectional optical scanner of the present invention detects the same test position of the tested breast twice in different directions. No matter where the tumor is located, it can be detected. Compared with structural images provided by conventional mammography, the present invention provides functional tomographic images of the breast so that diagnostic accuracy in the detection of breast cancer is improved.

Moreover, the higher the number of the light emitting elements of the light source module and the photosensors of the detection module of the first and the second optical detection modules, the denser the test positions of the tested breast. Thus the breast cancer diagnosis is more accurate.

Furthermore, the light emitting elements of the light source module and the photosensors of the detection module of the first and the second optical detection modules are arranged into an array for large-area detection, quick detection and reduced detection time.

In addition, the first and the second optical detection modules of the present invention are respectively disposed on a corresponding moving platform. The first movement module and the second movement module respectively control the movement of the first optical detection module and the second optical detection module in the X-direction and in the Y-direction. Thus the image shooting is not affected by the shape of the tested breast. Therefore the bidirectional optical scanner of the present invention is applied to breasts having various shapes for cancer detection.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A bidirectional optical scanner comprising:
   a first compression plate;
   a first optical detection module disposed over the first compression plate;
   the first optical detection module having at least one light source module and at least one detection module; the light source module including a plurality of light emitting elements arranged in a line; the detection module having a plurality of photosensors disposed in a line; one of the light emitting elements aligned with the corresponding photosensor to form a row;
   a second optical detection module arranged corresponding to the first optical detection module; the second optical detection module including at least one light source module and at least one detection module; the light source module having a plurality of light emitting elements arranged in a line and the detection module having a plurality of photosensors disposed in a line; one of the light emitting elements aligned with the corresponding photosensor to form a row; the light emitting elements of the light source module of the second optical detection module are corresponding to the photosensors of the detection module of the first optical detection module; the photosensors of the detection module of the second optical detection module are corresponding to the light emitting elements of the light source module of the first optical detection module; and
   a second compression plate arranged at the second optical detection module and located between the first optical detection module and the second optical detection module.

2. The device as claimed in claim 1, wherein the light emitting element is an optical fiber that emits laser light or broadband light.

3. The device as claimed in claim 2, wherein wavelength of the laser light or of the broadband light is near infrared wavelength.

4. The device as claimed in claim 1, wherein the bidirectional optical scanner further includes:
   a first movement module that is disposed with the first optical detection module and is used for control of movement of the first optical detection module; and
   a second movement module that is arranged with the second optical detection module and is used for control of movement of the second optical detection module.

5. The device as claimed in claim 4, wherein the first movement module includes:
   a first moving platform that is arranged with the first optical detection module and is used for control of movement of the first optical detection module in a first direction; and
   a second moving platform that is disposed with the first moving platform, perpendicular to the first moving platform, and used for control of movement of the first moving platform in a second direction;
   wherein the second movement module includes:
      a third moving platform that is arranged with the second optical detection module and is used for control of movement of the second optical detection module in the first direction; and
      a fourth moving platform that is disposed with the third moving platform, perpendicular to the third moving platform, and used for control of movement of the third moving platform in the second direction.

6. The device as claimed in claim 5, wherein the first moving platform includes:
   a first base;
   a first threaded rod that is disposed on the first base and the first optical detection module is arranged at the first threaded rod; and
   a driving device that is disposed on the first base and is connected to the first threaded rod so as to drive the first threaded rod and move the first optical detection module in the first direction.

7. The device as claimed in claim 6, wherein the first optical detection module further includes:
   a fastener having a first fixed end and a second fixed end; the light emitting elements of the light source module and the photosensors of the detection module are fixed on the first fixed end while the second fixed end is disposed on the first threaded rod of the first moving platform.

8. The device as claimed in claim 6, wherein the driving device is a servo motor.

9. The device as claimed in claim 6, wherein the second moving platform includes:
   a second base;
   two second threaded rods respectively disposed on each of two sides of the second base; and two ends of the first base are arranged at the two second threaded rods; and
   a driving device that is arranged at the second base and is connected to the second threaded rods to drive the second threaded rods and move the first moving platform in the second direction.

10. The device as claimed in claim 9, wherein the first moving platform further includes:
    two connection parts each of which having one end disposed on each of two ends of the first base and the other end arranged at each of the two second threaded rods.

11. The device as claimed in claim 9, wherein the driving device is a servo motor.

12. The device as claimed in claim 5, wherein the third moving platform includes:
    a third base;
    a third threaded rod that is disposed on the third base and the second optical detection module is arranged at the third threaded rod; and
    a driving device that is disposed on the third base and is connected to the third threaded rod so as to drive the third threaded rod and move the second optical detection module in the first direction.

13. The device as claimed in claim 12, wherein the second optical detection module further includes:
    a fastener includes a first fixed end and a second fixed end; the light emitting elements of the light source module and the photosensors of the detection module are fixed on the first fixed end while the second fixed end is disposed on the third threaded rod of the third moving platform.

14. The device as claimed in claim 12, wherein the driving device is a servo motor.

15. The device as claimed in claim 12, wherein the fourth moving platform includes:
    a fourth base;
    two fourth threaded rods respectively disposed on each of two sides of the fourth base; and two ends of the third base are arranged at the two fourth threaded rods; and
    a driving device that is arranged at the fourth base and is connected to the fourth threaded rods to drive the fourth threaded rods and move the third moving platform in the second direction.

16. The device as claimed in claim 15, wherein the third moving platform further includes:
two connection parts each of which having one end disposed on each of two ends of the third base and the other end arranged at each of the two fourth threaded rods.
17. The device as claimed in claim 15, wherein the driving device is a servo motor.
18. The device as claimed in claim 4, wherein the bidirectional optical scanner further includes:
a frame fixed on the first movement module and the first compression plate.
19. The device as claimed in claim 18, wherein the bidirectional optical scanner further including:
a fifth moving platform that is arranged with the frame so as to make the first movement module move in a third direction.
20. The device as claimed in claim 19, wherein the fifth moving platform includes:
a fifth base;
a fifth threaded rod that is disposed on the fifth base and the frame is set on the fifth threaded rod; and
a driving device that is connected to the fifth threaded rod and used for driving the fifth threaded rod and moving the first movement module in the third direction.
21. The device as claimed in claim 20, wherein the driving device is a servo motor.
22. A bidirectional optical scanner disposed on a mammography machine comprising:
a first movement module arranged at a first compression plate of the mammography machine;
a first optical detection module set on the first movement module;
a second movement module arranged at a loading platform of the mammography machine and corresponding to the first movement module;
a second optical detection module set on the second movement module; and
a second compression plate disposed on the second optical detection module;
wherein the first compression plate presses a breast set on the second compression plate, allowing the first optical detection module and the second optical detection module carrying out tests on the breast.
23. The device as claimed in claim 22, wherein the first movement module includes:
a first moving platform for mounting the first optical detection module and controlling movement of the first optical detection module in a first direction; and
a second moving platform disposed on the first moving platform, perpendicular to the first moving platform, and used for driving the first moving platform to move in a second direction;
wherein the second movement module includes:
a third moving platform for mounting the second optical detection module and controlling movement of the second optical detection module in the first direction; and
a fourth moving platform disposed on the third moving platform, perpendicular to the third moving platform, and used for driving the third moving platform to move in the second direction.
24. The device as claimed in claim 23, further including:
at least two connection parts respectively disposed on each of two sides of the second moving platform and fixed on the first compression plate so as to arrange the first movement module on the first compression plate.

25. The device as claimed in claim 23, further including:
a movement base disposed between the loading platform and the second movement module and used for moving the second movement module.
26. The device as claimed in claim 25, wherein the movement base includes:
a base for mounting the second movement module; and
two holding parts respectively arranged at each of two sides of the base.
27. The device as claimed in claim 23, wherein the first optical detection module including:
a fastener having a first fixed end and a second fixed end; the second fixed end is disposed on the first moving platform;
a light source module arranged at the first fixed end; and
a detection module set on the first fixed end.
28. The device as claimed in claim 27, wherein the first optical detection module further including:
a sliding block disposed on the first moving platform and the second fixed end of the fastener is arranged at the sliding block.
29. The device as claimed in claim 23, wherein the second optical detection module including:
a fastener having a first fixed end and a second fixed end; the second fixed end is disposed on the third moving platform;
a light source module arranged at the first fixed end; and
a detection module set on the first fixed end.
30. The device as claimed in claim 29, wherein the second optical detection module including:
a sliding block disposed on the third moving platform and the second fixed end of the fastener is arranged at the sliding block.
31. The device as claimed in claim 23, wherein the bidirectional optical scanner further includes:
a positioning mechanism set between the first moving platform and the third moving platform so as to position the first movement module and the second movement module.
32. The device as claimed in claim 31, wherein the positioning mechanism includes
a first positioning part in which one end thereof is disposed with a first clamping part that holds the first moving platform; and
a second positioning part in which one end thereof is connected slidingly to the first positioning part while the other end thereof is set with a second clamping part that holds the third moving platform.
33. The device as claimed in claim 31, wherein the bidirectional optical scanner further includes:
an assisted positioning mechanism that is arranged between the first moving platform and the third moving platform for assisting the positioning mechanism in positioning of the first movement module and the second movement module.
34. The device as claimed in claim 33, wherein the assisted positioning mechanism includes:
a first assisted positioning part whose one end is disposed with a first positioning part that is fixed on the first moving platform; and
a second assisted positioning part that is slidingly connected to the first assisted positioning part and having one end thereof disposed with a second positioning part that is fixed on the third moving platform.

35. The device as claimed in claim 34, wherein the assisted positioning mechanism further includes an alarm part set between the first assisted positioning part and the second assisted positioning part.

36. The device as claimed in claim 23, wherein the bidirectional optical scanner further includes a linear guideway positioning module disposed the third moving platform and used for positioning the second module on the loading platform of the mammography machine.

37. The device as claimed in claim 36, wherein the linear guideway positioning module includes:
 a linear guideway;
 a loading frame that is sliding within the linear guideway and is used for receiving the third moving platform; and
 two positioning parts that are respectively arranged at each of two ends of the linear guideway and fixed on each of two sides of the loading platform.

* * * * *